(12) United States Patent
Revell

(10) Patent No.: US 10,573,410 B2
(45) Date of Patent: Feb. 25, 2020

(54) MEDICAL IMAGING STUDY RETRIEVAL SYSTEM

(71) Applicant: Radia Inc. P.S., Lynnwood, WA (US)

(72) Inventor: David Revell, Lake Stevens, WA (US)

(73) Assignee: Radia Inc. P.S., Lynnwood, WA (US)

( * ) Notice: Subject to any disclaimer, the term of this patent is extended or adjusted under 35 U.S.C. 154(b) by 0 days.

(21) Appl. No.: 16/372,331

(22) Filed: Apr. 1, 2019

(65) Prior Publication Data

US 2019/0244705 A1 Aug. 8, 2019

Related U.S. Application Data

(63) Continuation of application No. 14/828,489, filed on Aug. 17, 2015, now Pat. No. 10,296,712, which is a continuation of application No. 13/796,133, filed on Mar. 12, 2013, now abandoned.

(60) Provisional application No. 61/729,263, filed on Nov. 21, 2012.

(51) Int. Cl.
*G16H 30/20* (2018.01)
*G06Q 50/24* (2012.01)
*G06F 19/00* (2018.01)
*G06T 7/00* (2017.01)
*G16H 10/60* (2018.01)
*G06F 16/50* (2019.01)

(52) U.S. Cl.
CPC .............. *G16H 30/20* (2018.01); *G06F 16/50* (2019.01); *G06F 19/321* (2013.01); *G06Q 50/24* (2013.01); *G06T 7/0014* (2013.01); *G16H 10/60* (2018.01); *G06T 2207/30096* (2013.01)

(58) Field of Classification Search
CPC ........ G06F 19/321; G06F 19/00; G06F 16/58; G06F 19/324; G06F 16/27; G06F 16/3331; G06F 16/3344; G06F 16/583; G06F 19/32; G16H 10/60; G16H 40/63; G16H 15/00; G16H 50/20; G16H 40/20; G16H 50/50; G16H 50/70; G06Q 10/10; G06Q 50/22; G06Q 50/24
See application file for complete search history.

(56) References Cited

U.S. PATENT DOCUMENTS

| | | |
|---|---|---|
| 2006/0115135 A1 | 6/2006 | Dehmeshki et al. |
| 2006/0239573 A1* | 10/2006 | Novatzky ........... G01S 7/52098 382/239 |
| 2009/0132499 A1* | 5/2009 | Yamagishi ............. G16H 50/70 |
| 2009/0287505 A1 | 11/2009 | Wood |
| 2012/0041786 A1 | 2/2012 | Yu |

* cited by examiner

*Primary Examiner* — Joseph D Burgess
(74) *Attorney, Agent, or Firm* — Perkins Coie LLP

(57) ABSTRACT

A programmed computer system receives an imaging study of the patient including metadata associated with the study. The metadata are analyzed to determine an anatomic region represented by the study. Additional imaging studies for the same patient are requested and the metadata associated with the additional studies are analyzed to determine relevant studies for the same or adjacent anatomic regions. Once the relevant prior studies have been identified, the computer requests the images associated with the identified prior imaging studies including the associated reports for review by a physician or other medical personnel.

12 Claims, 6 Drawing Sheets

MEDICAL IMAGING STUDY RETRIEVAL SYSTEM

CROSS-REFERENCE TO RELATED APPLICATIONS

The present application is a continuation of U.S. patent application Ser. No. 14/828,489, filed Aug. 17, 2015, titled MEDICAL IMAGEING STUDY RETRIEVAL SYSTEM, which is a continuation of U.S. patent application Ser. No. 13/796,133, filed on Mar. 12, 2013, and titled MEDICAL IMAGING STUDY RETRIEVAL SYSTEM, which claims priority to and the benefit of U.S. Patent Application No. 61/729,263, filed on Nov. 21, 2012 and titled MEDICAL IMAGING STUDY RETRIEVAL SYSTEM, all of which applications are incorporated by reference in their entireties.

FIELD OF THE TECHNOLOGY

The technology disclosed herein relates to medical information systems.

DETAILED DESCRIPTION OF THE PREFERRED EMBODIMENTS

Figure 1:
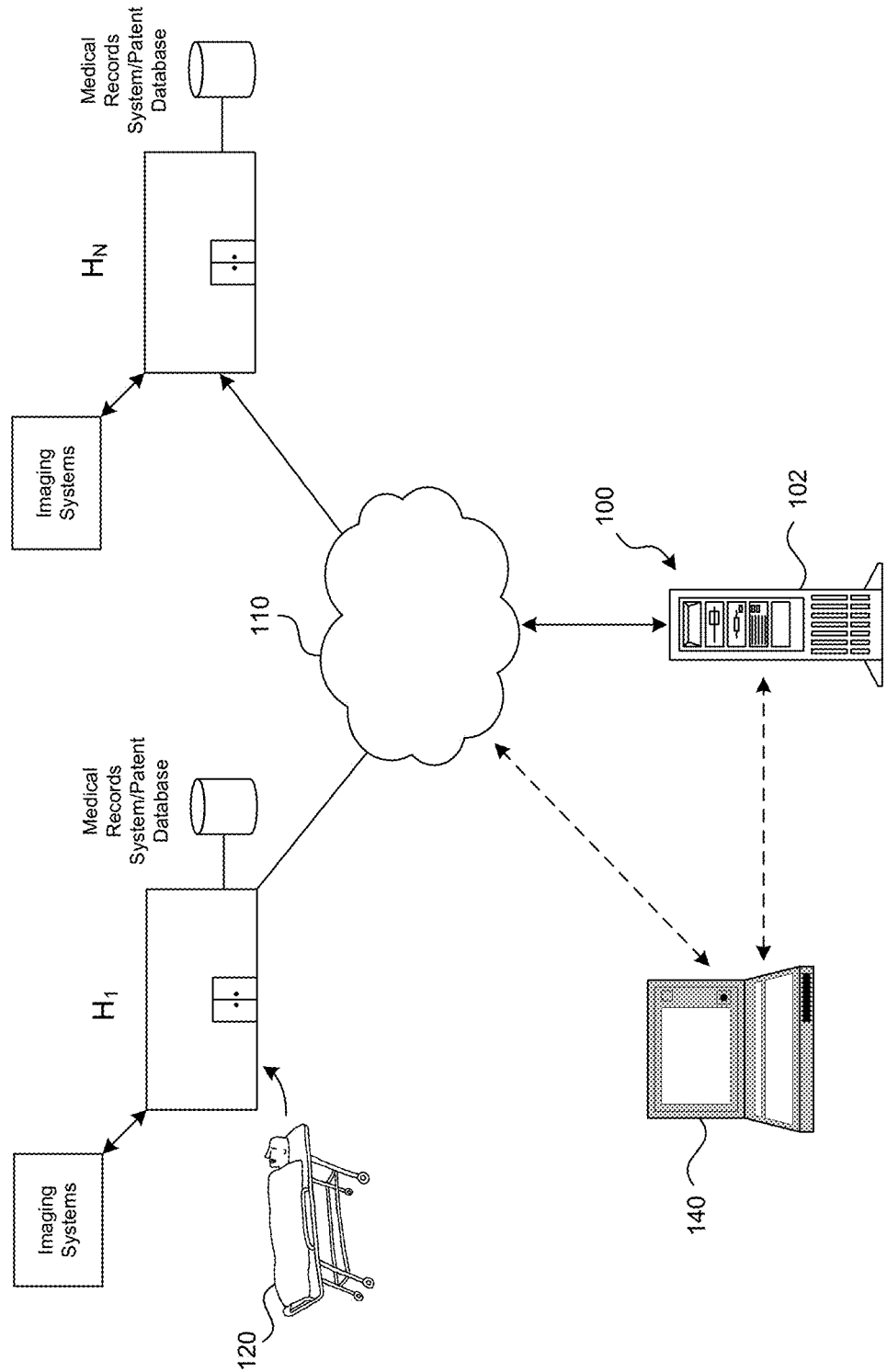
FIG. 1 illustrates an interconnected medical information system in which prior relevant imaging studies of a patient are determined and retrieved in accordance with an embodiment of the disclosed technology.

In order to accurately assess and diagnose a patient's condition, physicians often want to compare a patient's current examination results with examination results that were performed in the past. This is particularly true in radiology, whereby images of a patient's anatomy can be compared to prior images to determine growth of a tumor, healing of an injury or any other number of physiological changes that the physician considers in making their diagnosis and treatment recommendations.

One difficulty in reviewing prior imaging studies of a patient is that such studies may be stored across numerous computer systems associated with different hospitals, clinics, medical centers or the like. In addition, even if all of a patient's prior studies were located on the same computer system, there is currently no commonly accepted convention for indicating what portion of a patient's anatomy is represented by a study.

Most medical imaging studies are stored and transmitted electronically according to a DICOM (Digital Imaging and Communication in Medicine) standard. Currently the standard does not have an accepted protocol for specifying what portion of a patient's anatomy is represented in the study. While an imaging study typically has metadata associated with it, such metadata often does not specify the particular anatomy imaged. For example, a study of the patient's head may have metadata that includes the word "head" but may also include metadata that includes the names of adjacent body parts such as "neck" or "shoulder," or can include negative metadata keywords such as the words "not head.", or acronyms such as "HD" In the past, a physician, nurse or trained medical personnel would have to visually inspect each of the prior studies in order to retrieve all the prior imaging studies that are relevant to the current imaging study. Such a review can occupy a significant amount of time and thereby increases the overall cost of healthcare for the patient or insurance provider.

To address these problems and others, the technology disclosed herein relates to a computer system that is programmed to automatically retrieve relevant prior imaging studies from one or more computer systems on which such studies are stored. The computer systems may be connected on a single communication network or may be located on different communication networks.

In one embodiment, a computer system, such as a router computer, is programmed to analyze metadata associated with a received imaging study. The metadata is analyzed to determine a likely anatomic region represented in the imaging study based on a heuristic analysis of the metadata tags or entries. After the metadata has been analyzed, an imaging study is classified by its represented anatomic region. The router system then analyzes the metadata of the received imaging study for patient information such a patient identifier, code or even last name, first name etc. The router then sends a request to one or more PACS at the same or different medical facilities for metadata associated with prior imaging studies associated with the same patient.

The router analyzes the received metadata to classify the prior imaging studies according to the particular anatomic region depicted. Studies of the same anatomic region or adjacent regions are identified as being relevant to the current study. The router then requests that the images of the relevant imaging studies identified be sent to the router. In addition, the router requests that any reports associated with the identified relevant studies are also sent. Once the prior studies and associated reports are received, they can be stored and/or combined for easy access by a physician so that the physician can determine how a current imaging study relates to previous relevant imaging studies of the same or adjacent anatomic regions.

FIG. 1 illustrates a system for retrieving prior imaging studies of a patient in accordance with one embodiment of the disclosed technology. The system 100 includes a computer system 102 that is in communication with one or more medical information systems that may be located at hospitals or other medical facilities H1-HN. The computer system 102 may be located on the same communication network as the medical information systems of a single hospital (i.e. behind a firewall or other communication barrier). Alternatively, the computer 102 may be connected to the medical information systems via a wide area communication link such as the internet 110. In the example shown, a patient 120 visits the hospital H1 with a condition such as a head injury and is examined using any number of imaging modalities such as X-rays, CT scans, MRIs, ultrasound etc. In the example shown, the patient may receive a CT scan of their head from an imaging system operated by the hospital H1. The imaging study can then be forwarded through a communication link/internet 110 to the computer system 102 through conventional computer communication protocols. The communication protocols typically include appropriate security measures as required by the DICOM standard for handling a patient's confidential medical information. The retrieved imaging study is then available for a physician to view and analyze on their own computer system 140. The physician's computer system 140 may be directly connected to the computer 102 or may be remotely connected through the internet 110 or other computer communications network.

In order for the physician to diagnose a patient's condition, the physician may want to view prior imaging studies of the patient's anatomy or adjacent anatomy. These prior imaging studies may be located in one or more remotely located hospitals, clinics medical centers, doctor's office or the like.

As indicated above, current DICOM standards do not follow a conventional naming practice that identifies the particular anatomic region contained in an imagining study. Therefore, the computer system 102 analyzes metadata associated with the received imaging study to determine what anatomical region is represented. The computer system 102 then requests metadata associated with other prior imaging studies that were obtained for the same patient. The computer system 102 then analyzes the metadata that are associated with those studies to determine one or more relevant prior studies. In one embodiment, the studies that are determined to be relevant are those of the same or an adjacent anatomic region as the anatomic region depicted in the received or current imaging study. Once the prior relevant imaging studies have been identified, the computer system requests that the images associated with the identified studies be sent to the computer system 102 from the one or more hospitals H1-HN along with the reports that accompany those studies.

FIGS. 2-5 illustrate steps performed by the computer system 102 to classify a received imaging study to determine the anatomic region represented as well as to request prior relevant imaging studies.

Figure 2:
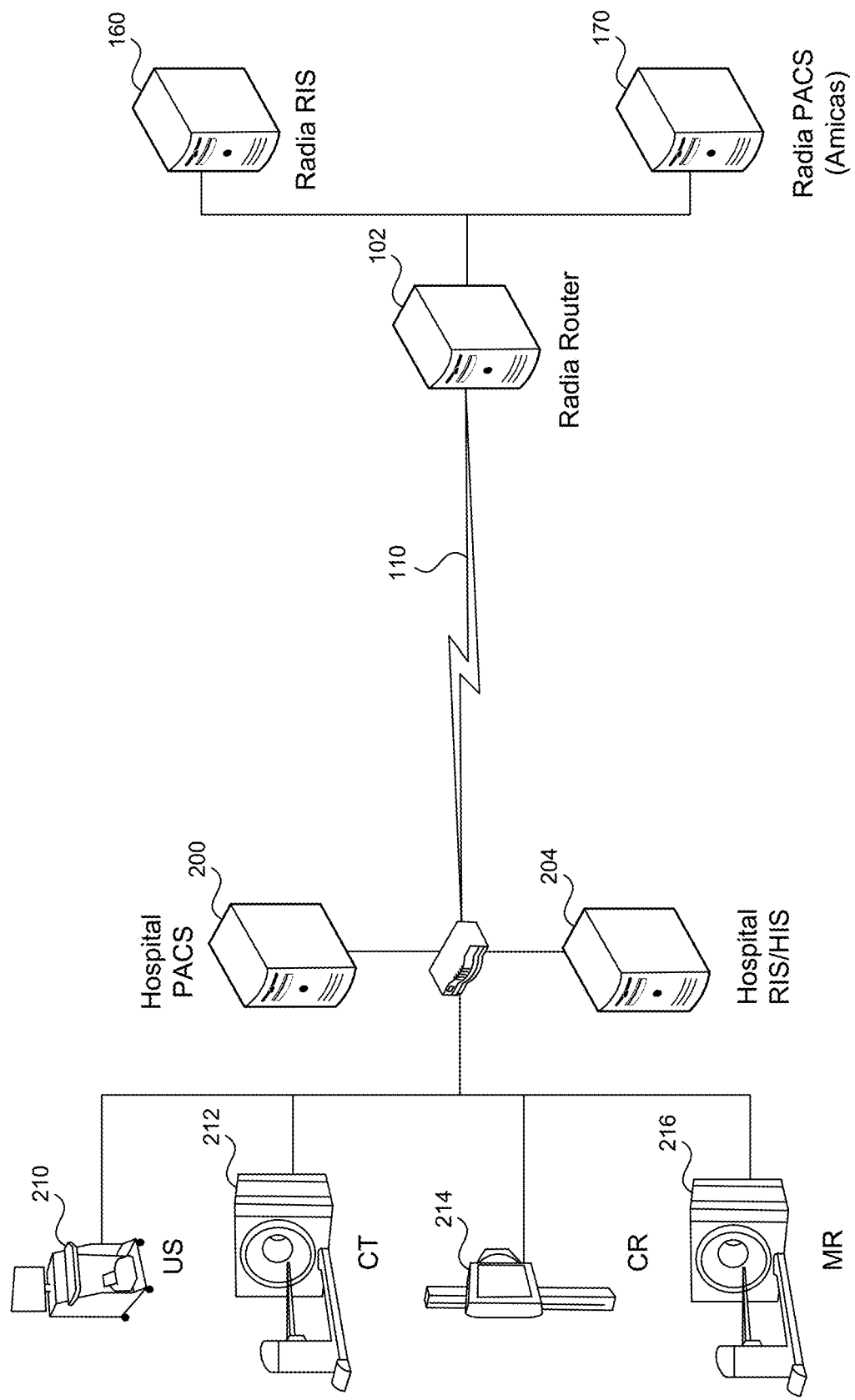
FIG. 2 illustrates a communication link set up between a router computer a hospital picture archive computer system (PACS) and a hospital information system (HIS) in accordance with an embodiment of the disclosed technology.

As shown in FIG. 2, the computer system 102, such a router computer may be in communication with other radiology information system (RIS) computers 160 or picture archive computer systems (PACS) 170 for storing the received imaging studies and reports. The computer system 102 is also connected via a computer communication link, such as the Internet 110, to computer systems associated with one or more hospitals or other medical facilities. Such computer systems typically include a hospital PACS 200 and hospital radiology information systems(RIS)/hospital information systems(HIS) 204. Together these computer systems store images and associated reports produced in response to studies performed with medical imaging equipment such as ultrasound machines 210, CT scanners 212, X-ray machines 214, magnetic resonance imaging (MRI) machines 216 or other similar systems.

Figure 3:
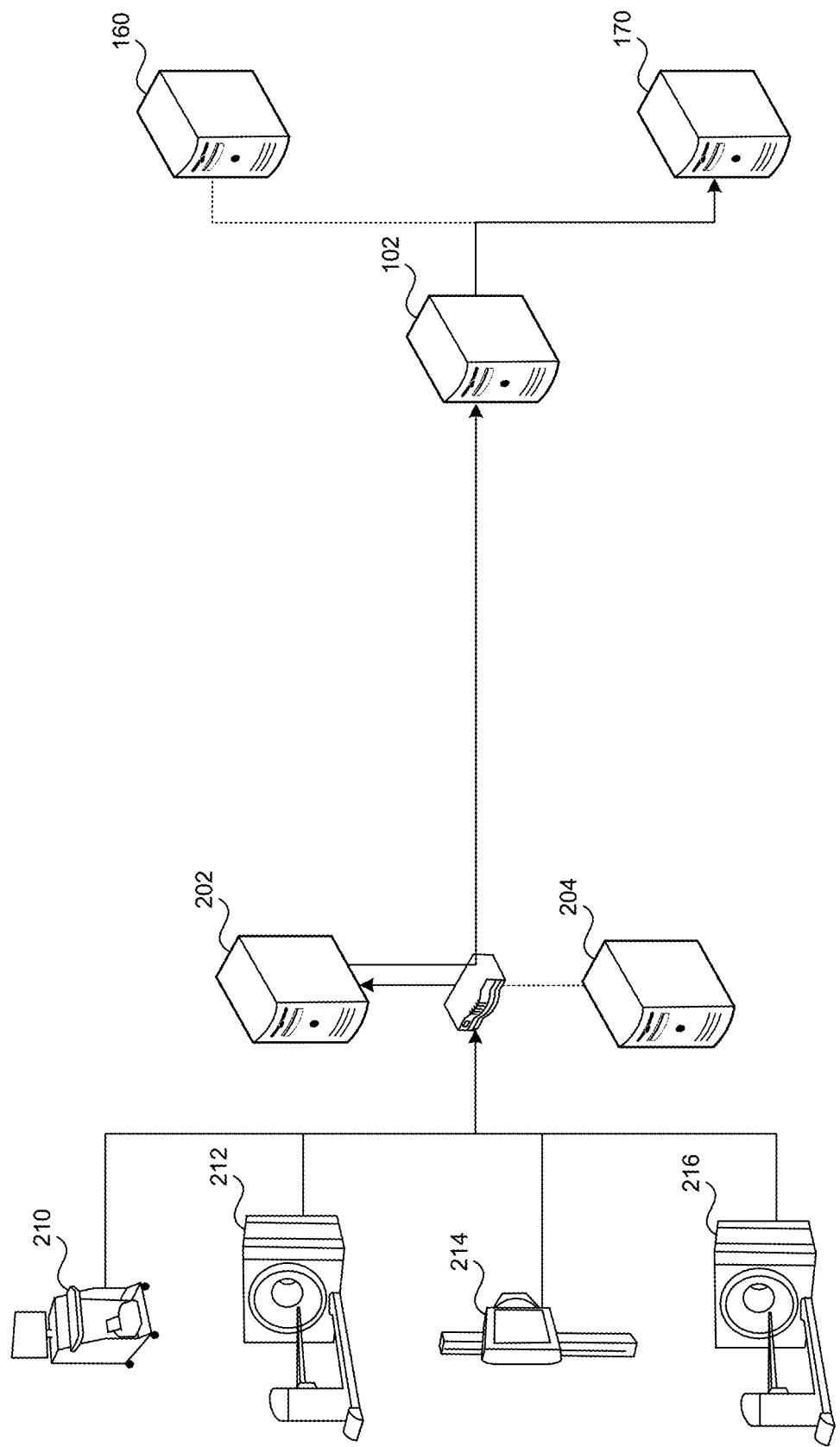
FIG. 3 illustrates how an imaging study is forwarded from a picture archive computer system at a hospital or other medical center to the router in accordance with an embodiment of the disclosed technology.

In the embodiment shown in FIG. 3, once an imaging study of a patient is complete, a technician (not shown) stores the study from one of the imaging machines to the hospital picture archive computer system 202. When the study is complete, it is sent by conventional means to the computer system 102. The study is typically sent via a secure private network point-to-point communications or VPN. Upon receipt of the current study by the computer system 102, the study may be forwarded for storage on the PACS 170.

Figure 4:
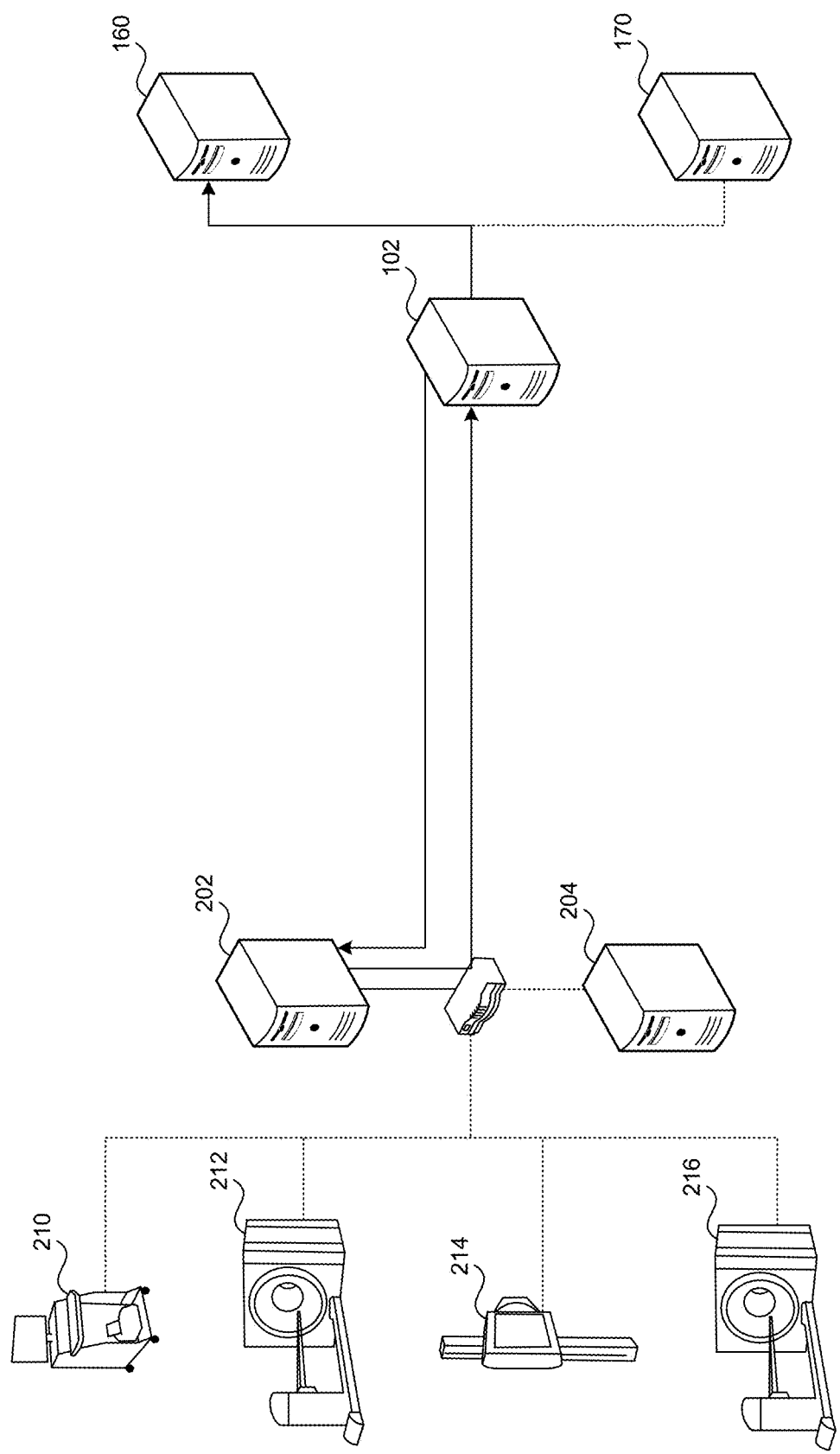
FIG. 4 illustrates how the router requests metadata for additional prior imaging studies based on a patient identifier retrieved from the received imaging study in accordance with an embodiment of the disclosed technology.

In the embodiment shown in FIG. 4, the computer system 102 analyzes metadata associated with the received study to determine a patient identifier, patient name or other code that uniquely identifies a particular patient. The computer system 102 then sends requests for the metadata associated with other prior imaging studies that are associated with the same patient. The metadata for prior imaging studies are returned from the hospital PACS system(s) 202 to the computer system 102 and can be stored on the RIS computer system 160.

Figure 5:
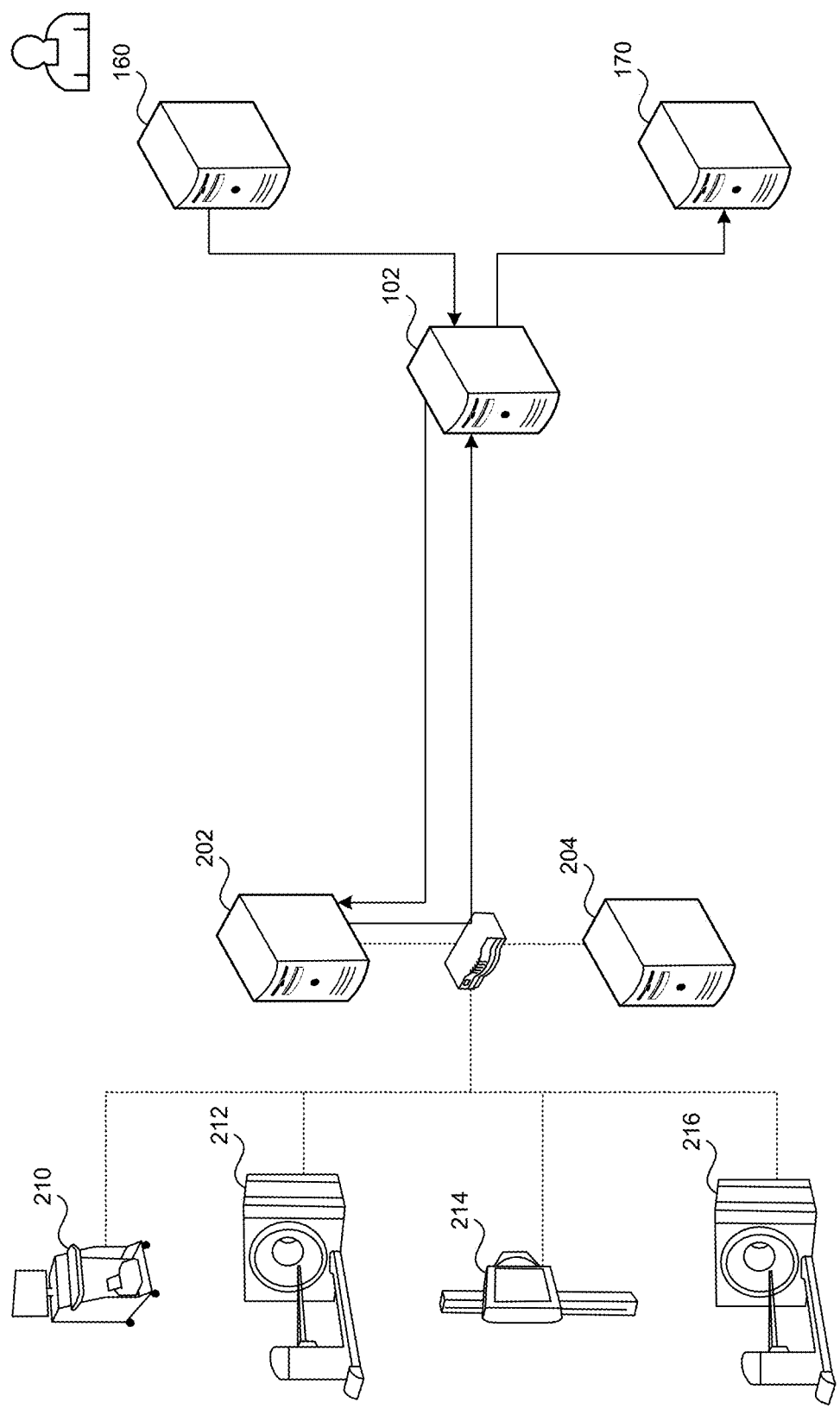
FIG. 5 illustrates how the router requests prior relevant imaging studies from one or more picture archive computer systems based on an analysis of received metadata in accordance with an embodiment of the disclosed technology.
Figure 6:
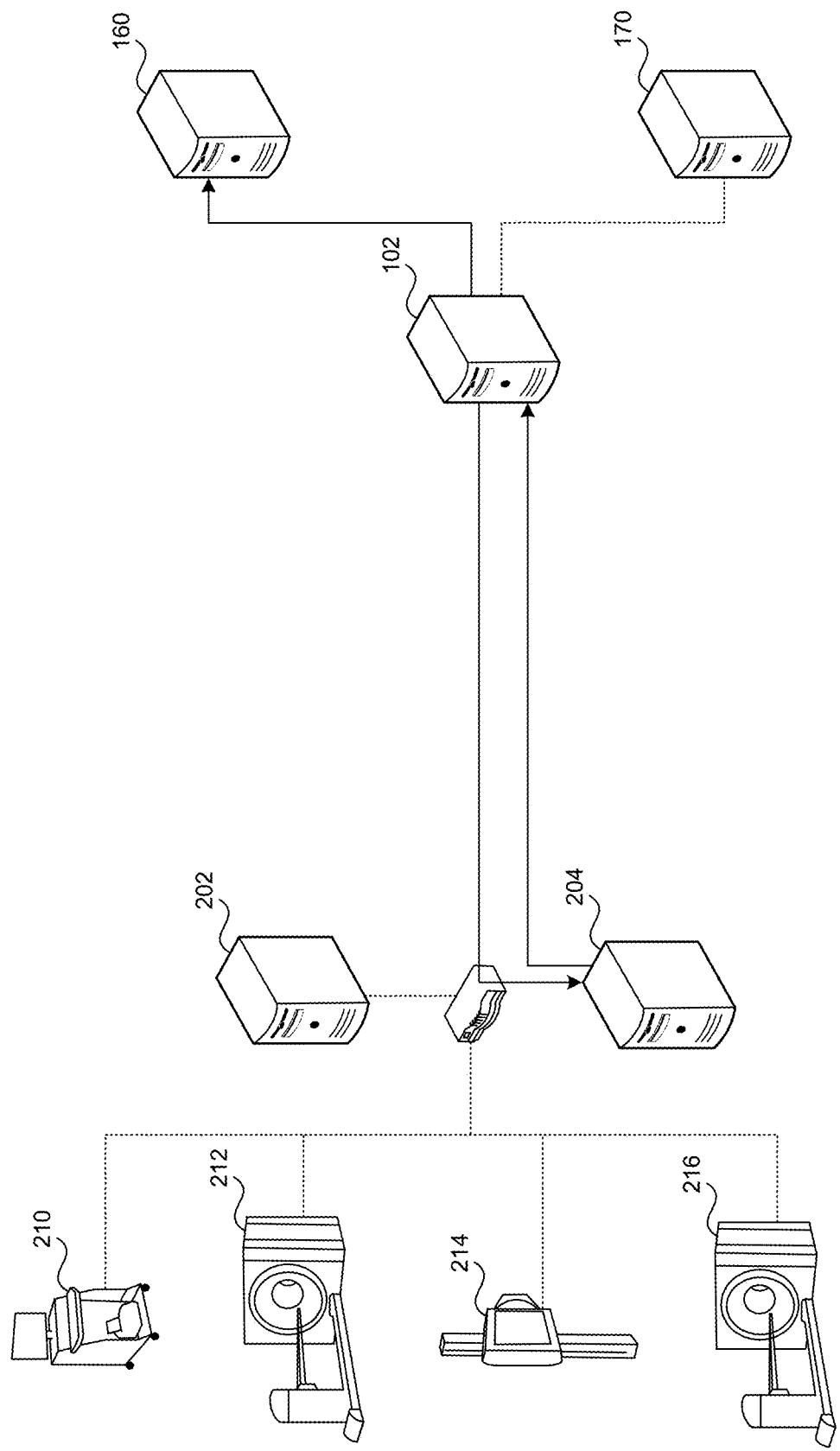
FIG. 6 illustrates how the router requests reports associated with the determined relevant patient imaging studies from one or more radiology information systems (RIS)/hospital information systems (HIS) in accordance with an embodiment of the disclosed technology.

In the embodiment shown in FIG. 5, the computer system 102 analyzes the received metadata to determine those studies that are relevant to the current imaging study. As will be explained in further detail below, the associated metadata is analyzed with one or more heuristics or programmed rules to determine which studies represent the same or adjacent anatomic regions as that represented in the current imaging study In the embodiment shown, the computer system 102 communicates with a single hospital PACS system 202. However we appreciated that the computer system may query multiple PACS or other medical information systems associated with other hospitals, clinics, doctor's offices or other locations where relevant prior imaging studies may be stored. Typically, the requests associated or sent to the other medical centers include an identifier of the patient such as their last name, middle initial, first name, date of birth, and sex as determined from the analysis of the metadata of the current imaging study.

In addition to requesting the images for the prior imaging studies of the same or adjacent anatomic regions that are determined by the computer system 102, a physician may also request images for specific prior imaging studies based on information in the patient's file or other information. A request for the images associated with the identified relevant and requested prior imaging studies is then sent to the hospital PACS 202 (and other medical information systems if appropriate). The images associated with these requested studies are then returned to the computer system 102 where they may be stored on the computer system 170.

The computer system 102 also requests any reports associated with the identified or requested prior imaging studies from the hospital RIS/HIS system(s). The received reports may be stored in the RIS computer 160. Once the appropriate imaging studies and associated reports have been received, they can be analyzed by the physician to diagnose the patient.

As indicated above, one embodiment of the disclosed technology analyzes the metadata associated with the current and prior imaging studies to determine likely anatomic areas represented by the studies. In one embodiment, the following heuristics are used to analyze the received metadata.

The body region (head, neck, chest, abdomen, pelvis, c spine, t spine, I spine, sacrum, wrist, forearm, elbow, humerus, shoulder, clavicle, sternum, foot, ankle, tibia/fibia, knee, femur, hip, lower extremity, upper extremity, hand, facial, breast, procedure, scrotum, pet, fetal, total body, vascular, etc) and modifier (left, right, bilateral) are determined by processing the Study Description DICOM tag through an algorithm that uses positive keywords, negative keywords, regular expressions, and keywords in relationship to spacing between words that are defined for each Body Region in a database.

In one embodiment, the computer system analyzes the Study Description tag specified by the DICOM protocol to determine the likely anatomical area represented by the study. How this tag is coded is not specified by the standard and can be manufacturer or hospital specific. For example, some hospitals or clinics may code the tag based on the charge master set up in the Hospital Information System (HIS) and is specific to each institution. In one embodiment, the computer system 102 takes the text of the Study Description tag and compares it to a database of positive and negative key words specified for each of the above-mentioned 33 body areas. For example, positive keywords for a head could include "head, cranium, skull, brain" while negative keywords for the head region could include "neck, sinus, shoulder" etc. Each body region may have +/−100 positive and negative keywords. The particular positive and negative keywords stored in a database for each region can be selected based on experience and testing.

The regular expressions are designed to determine both the presence of positive and negative keywords in the Study Description tag as well as their location. For example, the keyword "CAP" in the Body Region Chest, Abdomen, and Pelvis body regions has a regular expression to determine if the text is at the beginning, on either side of punctuation, or with spaces on either side of the Study description tag. In the Study Description Tag "HEAD/C-SPINE/CAP" is more indicative of the Chest, Abdomen, Pelvis body regions since "CAP" appears to the right of a "/" whereas "SCAPULA COMP" would not match since the text "CAP" is not at the beginning, on either side of punctuation, or has spaces on either side.

In one embodiment, the number of positive keyword hits compared to the number of negative keyword hits is compared for all the body regions. The result maybe something like Head (5 positive, 0 negative) Neck (3 positive, 0 negative) Chest (5 positive, 1 negative) etc. Using this example, the exam would be classified as a Head and Neck and Chest would be excluded.

The Study Description is processed through each Body Region's list of positive and negative key words to look for those relative key words while utilizing regular expressions and word position and spaces to determine a list of possible body regions. Those results of the negative keyword comparison are used to exclude regions. The Body Regions with the most positive keywords that have not been excluded using negative words are chosen as the body regions of the imaging study.

Adjacent Body Regions are defined in a database cross table comprising of the adjacent Body Regions. SubSpecialities are defined in a database cross table for matches of the DICOM Tag Modality (MR, CT, US, DX, RG, CR, XR, MG, etc.) and the chosen Body Regions.

Example 1: The study description ELBOW MIN 3 VWS-LT would be classified as an 'Elbow' body region, 'left' modifier. If the modality was an 'MR' the subspecialty would be 'MSK' but if the Modality was a 'DX, CR, XR, RG'; the subspecialty would be 'General'. The adjacent body region would be 'Forearm' and 'Humerus'.

Example 2: The study description 'CERVICAL SPINE' would be classified as a 'C Spine' body region and no modifier. If the modality was an 'MR' or 'CT' the subspecialty would be 'MSK' but if the Modality was a 'DX, CR, XR, and RG'; the subspecialty would be 'General'. The adjacent body region would be 'NECK', 'CHEST', 'T SPINE', 'HEAD', and 'BREAST.'

In one embodiment, the disclosed technology selects the top two closest prior imaging studies for retrieval for comparison against a current imaging study. In one embodiment, studies of adjacent anatomic regions obtained with the same imaging modality are selected over images of the same atomic region obtained with different imaging modalities. However, this may be user-selectable depending upon doctor preference. Particular anatomic regions that are adjacent to the anatomic region depicted in the current imaging study are selected based on rules or heuristics programmed into the computer system. Such heuristics may vary based on the age of the patient. For example in infants, images that can be classified as adjacent body parts may be different than those obtained from adults. Alternatively, the heuristics or rules may vary based on the sex of the patient.

As will be appreciated, the disclosed technology operates to automatically retrieve prior imaging studies and reports that may be useful by a physician or other medical provider in interpreting a current imaging study for the patient.

Although the embodiment of the disclosed technology is primarily directed to the use of the technology for radiologists, it will be appreciated that the technology can also be used by other healthcare providers such as dentists and pathology which use the DICOM standard for imaging. In addition, the technology is not limited to the treatment of humans. For example, the technology can also be applied to veterinary imaging studies.

In one embodiment, the disclosed technology is implemented using a sequence of stored program instructions that are executed by one or more processors contained within the computer system 102. These processors are typically programmed in any one of a number of well known programming languages such as C#, C++, VB, JAVA, SQL. The following pseudo-code listing illustrates one technique for the design and implementation of a number of software modules that perform the functions described above. Details of how a database is programmed in the computer system are set forth in detail in Appendix A.

Pseudo Code for Prior Imaging Study Retrieval System
Main Image Service
  Receives Dicom Images on port 104 for the current studies to be routed
  Updates the Properties Master Image Count
  Removes bad Dicom Tag 0x0009x0x1010
  Loops through active destination as defined in the OutBoundDestination table in the ClientRouter SQL database that is local to the router device.
    For each destination a new folder is created using the WorkingFolderPath as defined in the Properties table in the ClientRouter database with a subfolder of Main and another subfolder for each destination ID with a subfolder for each Study Instance ID
    Example
      D:\ClientRouterDicom\Main\DestinationID\StudyInstanceID\
    Each Dicom Images is written in to the corresponding destination\Study Instance ID folder named by the InstanceID +'.dcm'
    A Record is inserted in to the OutBoundQueue table in the ClientRouter Database for each destination\Study Instance ID combination
    The Properties table is updated by the Mainimage Size for each file added
    If these steps fail a Dicom Status Returns a status code of 1 to the sending Dicom Device A Copy of any SR objects is achieved off to the WorkingFolder\SR\StudyInstanceID\InstanceID.dcm folder
  The SR object is parsed out and inserted in to the ExamStructuredReport table
A Unique entry is inserted in to the ClientRouter FacilityStation table matching on CallingAE and IPAddress
The Study Description is passed in to a method that uses the keywords from the ClientRouter BodyRegion table to determine the exam body region
The Study Description is passed in to a method that uses the keywords from the ClientRouter Modifier table to determine the exam modifiers
The StudyDescription, Modality, BodyRegionID, ModifierID, and SubSpecialtyID is inserted in to the ClientRouter Exam table. The SubSpecialtyID is determined by using a combination lookup table in the ClientRouter SubSpecialityModalityBodyRegion table to match on Modality and BodyRegion to get the SubSpeciatlityID. This table is filled out via the Administrator tool.
A record is inserted in to the ClientRouter PriorRequestQueue table
A record is inserted in to the ClientRouterCentral Database PriorRequestQueue table via the PriorRequestServiceClient webservice which calls the ClientRouterCentral InsertPriorRequestQueue stored procedure that inserts the request for each router set up in the ClientRouterCentral PriorRequestRouters table by the original routerID.
A record is inserted in to the ClientRouter ExamDoseHistory table for information
A record is inserted in to the ClientRouter RecentStudyLog table and kept for 4 hours to prevent this study from being fetched as a prior if this patient has another study.

Main Image Forwarding Service
  Next available record to process is fetched via the ClientRouter LockOutBoundQueue Stored Procedure and is locked for professing.
  A new Thread is created to process the current record
    Data is fetched from the OutBoundQueue table
    The Last Write Time to the Record Folder Path is checked to see if greater than 5 seconds. If yes, it will continue to process. If No, the record is unlocked.
    Images are examined to have any denied SOPClasses as defined in the ClientRouter OutboundDestinations table in the DeniedSOPClasses field. The images with denied SOP Classes are moved to the WorkingFolder\BAD IMAGES\StudyInstanceID\SOPClass_InstanceID.dcm
    A Dicom Assotiation is initiated with ea of the Destination(s) and all of the remaining images are sent.
    Upon each image confirmed sent; the image will be deleted from the WorkingFolder\Main\DestinationID\StudyInstanceID\InstanceID.dcm folder.
    The folder is checked if there are any files remaining and if the file count=0 then the StudyInstanceID directory is deleted and the OutBoundQueue Record is deleted
    If files remain due to a failure; the OutboundQueue record is unlocked for a retry later Prior Scanner Service
  Next available record to process is fetched via the ClientRouter rad_LockPriorRequestQueue Stored Procedure and is locked for processing from the PriorRequestQueue table.
  A new Thread is created to process the current record
    Data is fetched from the PriorRequestQueue table
    The Body Regions and Modifier are looked up in the ClientRouter Exam table by Study Description and Modality
    The Adjacent Body Regions and Modifiers are looked up in the ClientRouter BodyRegionAdjacentRegions table
    If the PriorRequestQueue isSearchByPatientID is true
      The service does a dicom query back to the client PACS by Patiently and generates a list of prior exams
    If the PriorRequestQueue isSearchBy PatientID is false
      The service does a dicom query back to the client PACS by *PatientLastName* to pull all patients by the patient last name
      Those patients are filtered by the same birthdate and first letter of the first name.
      The service does another dicom query back to the PACS for each of the filtered patients by their patiently and generates a list of prior exams
    The list of prior studies is sorted by exam date descending
    The service passes the sorted list of prior studies to an algorithm to auto fetch the top 'X' studies.
      'X' is determined by the original study body region and the AutoFetchMax field in the BodyRegion table.
      That value then sets the MaxFetchCount in PriorRequestQueue table.
      The algorithm loops through the prior studies to determine the prior studies to automatically forward based on the modality, modifier, body region, adjacent body regions using the following criteria
        First Pass to get all Exams where the modality matches and is an exact body region match and modifiers match.
        Second Pass to get all Exams where the modality matches and is an adjacent body region and modifiers match.
        Third Pass to get all Exams where the Body Region is a match but different modalities and modifiers match.
        Forth Pass to get all Exams where the Modalities are different and the Body Region is Adjacent and modifiers match.
        Fifth Pass to get all Exams where the modality matches and is an exact body region match
        Sixth Pass to get all Exams where the modality matches and is an adjacent body region.
        Seventh Pass to get all Exams where the Body Region is a match but different modalities.
        Eighth Pass to get all Exams where the Modalities are different and the Body Region is Adjacent.
    The prior studies are inserted in to the PriorStudies table
      If successful the PriorRequestQueue record is deleted
      If the RequestedRouterID is set then the web service DeletePriorRequestQueueItem is called to delete the request in the ClientRouterCentral PriorRequestQueue table Another background thread processes the PriorStudies table
  Each record is locked using the rad_LockPriorStudy-ToCentralDB stored procedure
  The exam is inserted in to the RIS IAWorklistPriorExam table calling the webservice InsertIAWorklistPriorExam
  If successfully inserted;
    The PriorStudies table is updated DateInsertedCentralDB
    If the record is set to autofetch (GetStudy field), the record is inserted in to the PriorFetchQueue table
Another background thread cleans up records using the stored procedure rad_CleanUpPriorStudies every 5 seconds
  In the PriorStudies table that are DateInsertedCentralDB is not null and DateInsertedCentralDB is over 1 min old
  In the PriorFetchQueue table where the GetStudy is true and the DateCompleted is not null and the GetReport is true and the DateCompletedReport is not null
Prior Image Fetcher Service
  Next available record to process is fetched via the ClientRouter rad_LockPriorFetchStored Procedure and is locked for processing.
  A new Thread is created to process the current record
    The webservice UpdateIAWorklistPriorExamsExamProgress updates the IAWorklistPriorExam table that the study is inProcess
    A dicom query checks the destination PACS if the StudyInstanceID exists in the destination PACS
    If True
      The webservice UpdateIAWorklistPriorExamsExamProgress updates the IAWorklistPriorExam table that the study is inProcess=false, DateCompleted, DateLastAttempt, CompleteTypeID, and LastError
      The PriorFetchTable DateCompleted is updated
    If False
      A dicom move is issues from the source PACS to the Destination PACS
      If successful
        The webservice UpdateIAWorklistPriorExamsExamProgress updates the IAWorklistPriorExam table that the study is inProcess=false, DateCompleted, DateLastAttempt, CompleteTypeID, and LastError
        The PriorFetchTable DateCompleted is updated
      If failed
        The webservice UpdateIAWorklistPriorExamsExamProgress updates the IAWorklistPriorExam table that the study is inProcess=false, DateLastAttempt, and LastError
        The PriorFetchTable LastError, LastAttempt, inProcess is updated
  Timer refreshes the destinations in case the destination is in failover
Prior Image Server
  Receives Dicom Images on port 105
  Updates the Properties Master Image Count
  Removes bad Dicom Tag 0x0009x0x1010
  Loops through active destination as defined in the OutBoundDestination table in the ClientRouter SQL database that is local to the router device.
    For each destination a new folder is created using the WorkingFolderPath as defined in the Properties table in the ClientRouter database with a subfolder of Main and another subfolder for each destination ID with a subfolder for each Study Instance ID
      Example     D:\ClientRouterDicom\Priors\1\Study InstanceID\
    Each Dicom Images is written in to the corresponding destination\Study Instance ID folder named by the InstanceID+'.dcm'
    A Record is inserted in to the OutBoundQueue table in the ClientRouter Database for each destination\Study Instance ID combination
    The Properties table is updated by the MainImage Size for each file added
    If these steps fail a Dicom Status Returns a status code of 1 to the sending Dicom Device
  A Copy of any SR objects is achieved off to the WorkingFolder\SR\StudyInstanceID\InstanceID.dcm folder
    The SR object is parsed out and inserted in to the ExamStructuredReport table
  A Unique entry is inserted in to the ClientRouter FacilityStation table matching on CallingAE and IPAddress
  The Study Description is passed in to a method that uses the keywords from the ClientRouter BodyRegion table to determine the exam body region
  The Study Description is passed in to a method that uses the keywords from the ClientRouter Modifier table to determine the exam modifiers
  The StudyDescription, Modality, BodyRegionID, ModifierID, and SubSpecialtyID is inserted in to the ClientRouter Exam table. The SubSpecialtyID is determined by using a combination lookup table in the ClientRouter SubSpecialityModalityBodyRegion table to match on Modality and BodyRegion to get the SubSpeciatlityID. This table is filled out via the Administrator tool.
  A record is inserted in to the ClientRouter RecentStudyLog table and kept for 4 hours to prevent this study from being fetched as a prior if this patient has another study.
Prior Image Forwarder Service
  Next available record to process is fetched via the ClientRouter rad_LockPriorImageQueue Stored Procedure and is locked for processing.
  A new Thread is created to process the current record
    Data is fetched from the PriorImageQueue table
    The Last Write Time to the Record Folder Path is checked to see if greater than 5 seconds. If yes, it will continue to process. If No, the record is unlocked.
    Images are examined to have any denied SOPClasses as defined in the ClientRouter OutboundDestinations table in the DeniedSOPClasses field. The images with denied SOP Classes are moved to the WorkingFolder\BAD IMAGES\Study InstanceID\SOPClass_InstanceID.dcm
    A Dicom Assotiation is initiated with ea of the Destination(s) and all of the remaining images are sent.
    Upon each image confirmed sent; the image will be deleted from the WorkingFolder\Priors\DestinationID\StudyInstance ID \InstanceID.dcm folder.
    The folder is checked if there are any files remaining and if the file count=0 then the StudyInstanceID directory is deleted and the PriorImageQueue Record is deleted
    If files remain due to a failure; the PriorImageQueue record is unlocked for a retry later MonitorCentralPriorStudiesService:
  Every second the service calls the webservice GetIAWorklistPriorExamsToProcess for the individual router ID and returns a collection of exam objects. The GetIAWorklistPriorExamsToProcess calls the RIS database GetIAWorklistPriorExamsToProcess Stored Procedure to fetch all data from the IAWorklistPriorExams table where the routerID matches and the GetStudy=true and InProcess=false and DateStarted is null
  If the collection count is greater than 0 the exams are inserted in to the ClientRouter rad_InsertPriorStudiesManualRequest which inserts the exams in to the PriorFetchQueue table
Monitor CentralPriorRequests
  Every second the service calls the webservice GetPriorRequests by that routerID. The GetPriorRequests call the ClientRouterCentral database GetPriorRequestQueue stored procedure that gets the top 100 records from the ClientRouterCentral PriorRequestQueue table where the RequstedRouterID matches and the DateRouterDownloaded is null
  If the collection count is greater than 0 the exams are inserted in to the ClientRouter rad_InsertPriorRequestQueue which inserts the exams in to the PriorRequestQueue Table
Prior Report Fetcher Service
  Next available record to process is fetched via the ClientRouter rad_LockPriorReportFetchStored Procedure and is locked for processing for all prior exams requested.
  A new Thread is created to process the current record
    Data is fetched from the ClientRouter.PriorFetchQueue table for the record.
    The webservice UpdateIAWorklistPriorExamsReportProgress is called to update the progress on the central RIS.IAWorklistPriorExams table
    The ReportSystemTypeID is determined from the ClientRouter.Facility table which assigns a facilityID but the unique IPAddress/AE Title combination,
    Depending on the ReportSystemTypeID (EPIC, GE RIS/IC, MEDITECH), the prior report, dictated by, and dictated date are returned.
    The report is formatted to monospace text
    The report, dictated by, dictated date are updated in the RIS.IAWorklistPriorExam table via the webservice UpdateIAWorklistPriorExamReport.
  Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.
  A computer storage medium can be, or can be included in, a computer-readable non-transitory storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "programmed processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode), or OLED (organic light emitting diode) monitor, for displaying information to the user and a keyboard and a pointing device, e.g., a mouse or a trackball, by which the user can provide input to the computer. In some implementations, a touch screen can be used to display information and to receive input from a user. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e,g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include any number of clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

I claim:

1. A computer system for retrieving imaging studies of a patient, comprising:
   a memory that stores a sequence of program instructions;
   a processor configured to execute the instructions in order to:
   receive a first imaging study of a patient, the first imaging study performed with a medical imaging machine operated at a first medical facility;
   analyze metadata associated with the first imaging study to identify the patient and to identify an anatomic region depicted in the imaging study;
   send a request for metadata for prior imaging studies performed on the patient to at least a second medical facility remote from the first medical facility;
   receive metadata for one or more prior imaging studies performed on the patient;
   store a number of positive and negative keywords for each of a number of different anatomic regions;
   analyze a DICOM study description tag contained in the metadata for the one or more prior imaging studies to determine a result for each of the number of different anatomic regions based on the presence of the positive and negative keywords for the anatomic regions in the DICOM study description tag for the one or more prior imaging studies;
   select, based on the result for each of the number of different anatomic regions, at least one prior relevant imaging study that is for an anatomic region that is the same as, or adjacent to, the anatomic region identified in the received first imaging study;
   request images and associated reports for the at least one prior relevant imaging study;
   receive the images and the associated reports for the at least one prior relevant imaging study; and
   display at least one of the received images and the associated reports for the at least one relevant imaging study.

2. A non-transitory computer readable media having instructions stored thereon that are executable by a processor to retrieve prior imaging studies of a patient, by:
   receiving an a first imaging study of a patient, the imaging study performed with a medical imaging machine operated at a first medical facility;
   analyzing metadata associated with the first imaging study to identify the patient and to identify an anatomic region depicted in the imaging study;
   sending a request for metadata for prior imaging studies performed on the patient to at least a second medical facility remote from the first medical facility;
   receiving metadata for one or more prior imaging studies performed on the patient;
   storing a number of positive and negative keywords for each of a number of different anatomic regions;
   analyzing a DICOM study description tag contained in the metadata for the one or more prior imaging studies to determine a result for each of the number of different anatomic regions based on the presence of the positive and negative keywords for the anatomic regions in the DICOM study description tag;
   selecting, based on the result for each of the number of different anatomic regions, at least one prior relevant imaging study that is for an anatomic region that is the same as, or adjacent to, the anatomic region identified in the received first imaging study;
   requesting images and associated reports for the at least one prior relevant imaging study;
   receiving the images and the associated reports for the at least one prior relevant imaging study; and
   displaying at least one of the received images and the associated reports for the at least one prior relevant imaging study.

3. The computer system of claim 1 wherein the medical imaging machine is selected from the group consisting of a CT scanner machine, an X-ray machine, a magnetic resonance imaging (MRI) machine, and an ultrasound machine.

4. The computer system of claim 1 wherein the processor is configured to execute the instructions in order to the determine the location of the positive and negative keywords in the DICOM study description tag to determine the result for each of the number of different anatomic regions.

5. The computer system of claim 1, wherein the processor is configured to execute instructions to compare the number of positive keywords versus the number of negative keywords in a DICOM study description tag to identify one or more relevant prior imaging studies.

6. A computer system for retrieving imaging studies of a patient, comprising:
  a memory that stores a sequence of program instructions;
  a processor configured to execute the instructions in order to:
    analyze metadata associated with a first imaging study to identify a patient and to identify an anatomic region depicted in the first imaging study;
    send a request for metadata for prior imaging studies performed on the patient;
    receive metadata for one or more prior imaging studies performed on the patient;
    analyze DICOM study description tags contained in the metadata for the one or more prior imaging studies to determine a result for each of the number of different anatomic regions based on the presence of the positive and negative keywords for the anatomic regions in the DICOM study description tag;
    select, based on the result for each of the number of different anatomic regions, at least one prior relevant imaging study that is for an anatomic region that is the same as, or adjacent to, the anatomic region identified in the first imaging study;
    request images for the at least one prior relevant imaging study;
    and receive the images for the at least one prior relevant imaging study.

7. The computer system of claim 6, wherein the processor is configured to execute instructions to analyze a DICOM study description tag with a regular expression to determine the presence or absence of one or more positive and negative keywords in the study description tag and the location of the positive and negative keywords in the study description tag to determine the result for each of the number of different anatomic regions.

8. The computer system of claim 6, wherein the processor is configured to execute instructions to compare the number of positive keywords versus the number of negative keywords in the study description tag when determining a result for each of the number of different anatomic regions.

9. The computer system of claim 6, wherein the processor is configured to execute instructions to send the request for metadata for prior imaging studies to a remote computer system and to receive images for at least one prior relevant imaging study from the remote computer system.

10. A computer readable media with instructions that are executable by a processor of a computer system to recall relevant imaging studies of a patient by:
  analyzing metadata associated with a first imaging study to identify the patient and to identify an anatomic region depicted in the first imaging study;
  sending a request for metadata for prior imaging studies performed on the patient;
  receiving metadata for one or more prior imaging studies performed on the patient;
  analyzing DICOM study description tags contained in the metadata for the one or more prior imaging studies to determine a result for each of the number of different anatomic regions based on the presence of the positive and negative keywords for the anatomic regions in the DICOM study description tag;
  selecting, based on the result for each of the number of different anatomic regions, at least one prior relevant imaging study that is for an anatomic region that is the same as, or adjacent to, the anatomic region identified in the first imaging study;
  requesting images for the at least one prior relevant imaging study;
  and receiving the images for the at least one prior relevant imaging study.

11. The computer readable media of claim 10, further including instructions that are executable by a processor to analyze a DICOM study description tag with a regular expression to determine the presence or absence of one or more positive and negative keywords in the study description tag and the location of the positive and negative keywords in the study description tag to determine the result for each of the number of different anatomic regions.

12. The computer readable media of claim 10, further including instructions that are executable by a processor to compare the number of positive keywords versus the number of negative keywords in the study description tag when determining the result for each of the number of different anatomic regions.

* * * * *

UNITED STATES PATENT AND TRADEMARK OFFICE
CERTIFICATE OF CORRECTION

PATENT NO. : 10,573,410 B2
APPLICATION NO. : 16/372331
DATED : February 25, 2020
INVENTOR(S) : David Revell Page 1 of 1

It is certified that error appears in the above-identified patent and that said Letters Patent is hereby corrected as shown below:

In the Specification

In Column 4, Line 24, delete "study" and insert -- study. --, therefor.

In Column 5, Line 58, delete "'left'" and insert -- 'Left' --, therefor.

In Column 6, Line 64, delete "Mainimage" and insert -- MainImage --, therefor.

In Column 8, Line 15, delete "Patiently" and insert -- PatientID --, therefor.

In Column 8, Line 25, delete "patiently" and insert -- patientID --, therefor.

In Column 11, Lines 7-8, delete "Exarns" and insert -- Exams --, therefor.

In Column 11, Line 40, delete "combination," and insert -- combination. --, therefor.

In Column 13, Line 28, delete "e,g.," and insert -- e.g., --, therefor.

In the Claims

In Column 14, Line 33, in Claim 2, delete "an a" and insert -- a --, therefor.

Signed and Sealed this
Twenty-sixth Day of May, 2020

Andrei Iancu
*Director of the United States Patent and Trademark Office*